United States Patent
Bassler et al.

(10) Patent No.: US 7,332,634 B2
(45) Date of Patent: Feb. 19, 2008

(54) METHOD FOR THE CONTINUOUS PURIFICATION BY DISTILLATION OF 1,2-PROPYLENE GLYCOL THAT ACCUMULATES DURING THE SYNTHESIS OF PROPYLENE OXIDE WITHOUT COUPLING PRODUCTS

(75) Inventors: Peter Bassler, Viernheim (DE); Hans-Georg Goebbel, Kallstadt (DE); Joaquim Henrique Teles, Otterstadt (DE); Peter Rudolf, Ladenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 262 days.

(21) Appl. No.: 10/521,783

(22) PCT Filed: Jul. 22, 2003

(86) PCT No.: PCT/EP03/07985

§ 371 (c)(1),
(2), (4) Date: Jan. 21, 2005

(87) PCT Pub. No.: WO2004/009571

PCT Pub. Date: Jan. 29, 2004

(65) Prior Publication Data

US 2005/0250965 A1    Nov. 10, 2005

(30) Foreign Application Priority Data

Jul. 23, 2002  (DE) .................... 102 33 382

(51) Int. Cl.
*C07C 27/28*  (2006.01)
*C07C 29/74*  (2006.01)
*C07C 31/20*  (2006.01)

(52) U.S. Cl. ..................... 568/868; 568/699
(58) Field of Classification Search ........... None
See application file for complete search history.

(56) References Cited

U.S. PATENT DOCUMENTS 2,471,134 A  5/1949  Wright
3,574,772 A  4/1971  Becker et al.
4,230,533 A  10/1980  Giroux
6,479,680 B1 *  11/2002  Bassler et al. .............. 549/529

FOREIGN PATENT DOCUMENTS

| DE | 196 23 609 | 12/1997 |
|---|---|---|
| DE | 197 23 949 | 12/1998 |
| DE | 101 05 527 | 8/2002 |
| EP | 0 122 367 | 10/1984 |
| EP | 0 126 288 | 11/1984 |
| EP | 0 133 510 | 2/1985 |
| WO | 99/31034 | 6/1999 |
| WO | 00/07965 | 2/2000 |

OTHER PUBLICATIONS

Kaibel, Gerd. "Distillation Columns with Vertical Partitions", Chem. Eng. Technol., vol. 10, pp. 92-98 1987.
Elm, Rainer et al. "Propandiole", Ullmanns Encyklopaedie der technischen Chemie, Verlag Chemie, 4th edition, vol. 19, pp. 425-432 1980.
Kaibel, Gerd et al. "Gestaltung destillativer Trennungen unter Einbeziehung thermodynamischer Gesichtspunkte", Chem.-Ing.-Tech., vol. 61, No. 1, pp. 16-25, with English abstract 1989.
Kaibel, G. et al. "Thermodynamics—guideline for the development of distillation column arrangements", Gas Separation & Purification, vol. 4, pp. 109-114 1990.
"Distillation's great leap forward?" Process Engineering, vol. 2, pp. 33-34 1993.
Lestak, F. et al. "Heat Transfer Across the Wall of Dividing Wall Columns", Trans IChemE, vol. 72, part A, pp. 639-644 1994.
Lestak, Frigyes et al. "Advanced Distillation Saves Energy & Capital", Chemical Engineering, vol. 7, pp. 72-76 1997.
"Production", Hydrogen Peroxide, Ullmann's Encyclopedia of Industrial Chemistry, 5th ed., vol. 13, pp. 447-456, 1996.

* cited by examiner

*Primary Examiner*—Brian Davis
(74) *Attorney, Agent, or Firm*—Oblon, Spivak, McClelland, Maier & Neustadt, P.C.

(57) ABSTRACT

The invention relates to a continuously operated process for the purification by distillation of the 1,2-propylene glycol formed as by-product in the synthesis of propylene oxide, wherein the mixture formed in the synthesis which contains the 1,2-propylene glycol is separated in a dividing wall column into low-, intermediate- and high-boiling fractions and the 1,2-propylene glycol is taken off as intermediate boiler at the side offtake of the column.

17 Claims, 3 Drawing Sheets

METHOD FOR THE CONTINUOUS PURIFICATION BY DISTILLATION OF 1,2-PROPYLENE GLYCOL THAT ACCUMULATES DURING THE SYNTHESIS OF PROPYLENE OXIDE WITHOUT COUPLING PRODUCTS

This application is a 371 of PCT/EP03/07985, filed Jul. 22, 2003.

BACKGROUND OF THE INVENTION

1. Field of the Invention

The present invention relates to a continuously operated process for the purification by distillation of the 1,2-propylene glycol formed as by-product in the preferably coproduct-free synthesis of propylene oxide, in which the mixture formed in the synthesis which contains the 1,2-propylene glycol is separated in a dividing wall column into low-, intermediate- and high-boiling fractions and the 1,2-propylene glycol is taken off as intermediate boiler from the side offtake of the column.

2. Discussion of the Background

In the customary processes of the prior art, propylene oxide can be prepared by reaction of propylene with hydroperoxides, and these reactions can be carried out in one or more stages.

For example, the multistage process described in WO 00/07965 for preparing propylene oxide by reacting propylene with a hydroperoxide is carried out according to a reaction scheme comprising at least the steps (i) to (iii):
(i) reaction of the hydroperoxide with propylene to give a product mixture comprising propylene oxide and unreacted hydroperoxide,
(ii) separation of the unreacted hydroperoxide from the mixture resulting from step (i),
(iii) reaction of the hydroperoxide which has been separated off in step (ii) with propylene.

Accordingly, the reaction of propylene with the hydroperoxide takes place in at least two steps (i) and (iii), with the hydroperoxide separated off in step (ii) being reused in the reaction.

The reactions in steps (i) and (iii) are preferably carried out in two separate reactors, preferably fixed-bed reactors, with the reaction of step (i) preferably taking place in an isothermal reactor and the reaction of step (iii) taking place in an adiabatic reactor.

The hydroperoxide used in this sequence is preferably hydrogen peroxide, and propylene is preferably brought into contact with a heterogeneous catalyst during the reaction which is carried out in methanol as solvent.

Here, the hydrogen peroxide conversion in step (i) is from about 85% to 90% and that in step (iii) is about 95% based on step (ii). Over both steps, a total hydrogen peroxide conversion of about 99% can be achieved at a propylene oxide selectivity of about 94-95%.

Owing to the high selectivity of the reaction, the synthesis is also referred to as coproduct-free oxirane synthesis.

As secondary reactions in the formation of propylene oxide, subsequent reactions of the propylene oxide with methanol, water and hydrogen peroxide take place, giving products having boiling points higher than that of propylene oxide. As reaction by-products, methoxypropanols are formed by addition of methanol onto propylene oxide, 1,2-propylene glycol, dipropylene glycol and tripropylene glycol are formed by addition of water and 2-hydroperoxy-1-propanol and 1-hydroperoxy-2-propanol are formed by addition of hydrogen peroxide. Preference is given to reducing the hydroperoxy alcohols, which likewise forms 1,2-propylene glycol. For example, it is possible to use the methods described in DE 101 05 527.7 for the reduction.

After the methanol solvent has been separated off and recirculated, the reaction by-products remain in the wastewater and can be isolated therefrom as a secondary yield.

A particular material of value present in the wastewater is 1,2-propylene glycol which has a variety of applications. For example, it can be used for preparing polyether alcohols, as esterification component in polyester syntheses, for the preparation of polyurethanes, as reactive solvent for syntheses of polyurethanes for use in coatings and paints/varnishes or as film formation aid. High-purity propylene glycol is otherwise produced industrially by reaction of propylene oxide with water at pressures of from 15 to 25 bar and a temperature of from 180 to 220° C. The work-up is complicated, since three columns connected in series have to be used for separating off the propylene glycol (Ullmann's Encyclopädie der technischen Chemie, Verlag Chemie, 4th Edition, pages 425 to 431). However, all possible processes for the catalytic addition of water onto propylene oxide can be used for the preparation of propylene glycol, for example the method described in WO 99/31034.

To separate off the propylene glycol from the wastewater obtained in the preparation of propylene oxide, separation processes employed hitherto make use of distillation columns having a side offtake or columns connected in series. However, this procedure, too, requires relatively complicated apparatus and a relatively high energy consumption, which is uneconomical. For this reason, the isolation of this material of value is frequently omitted and the wastewater in which it is present is passed to incineration.

SUMMARY OF THE INVENTION

It is an object of the present invention to optimize the separation by distillation of the 1,2-propylene glycol formed as by-product in the reaction of propylene with hydroperoxides to produce propylene oxide and present in the wastewater stream so as to achieve a decrease in the otherwise usual energy consumption.

We have found that this object is achieved by a continuously operated process for the purification of the 1,2-propylene glycol formed as by-product in the preferably coproduct-free synthesis of propylene oxide and present in the wastewater stream by distillation using a dividing wall column.

DETAILED DESCRIPTION OF THE INVENTION

Figure 1:
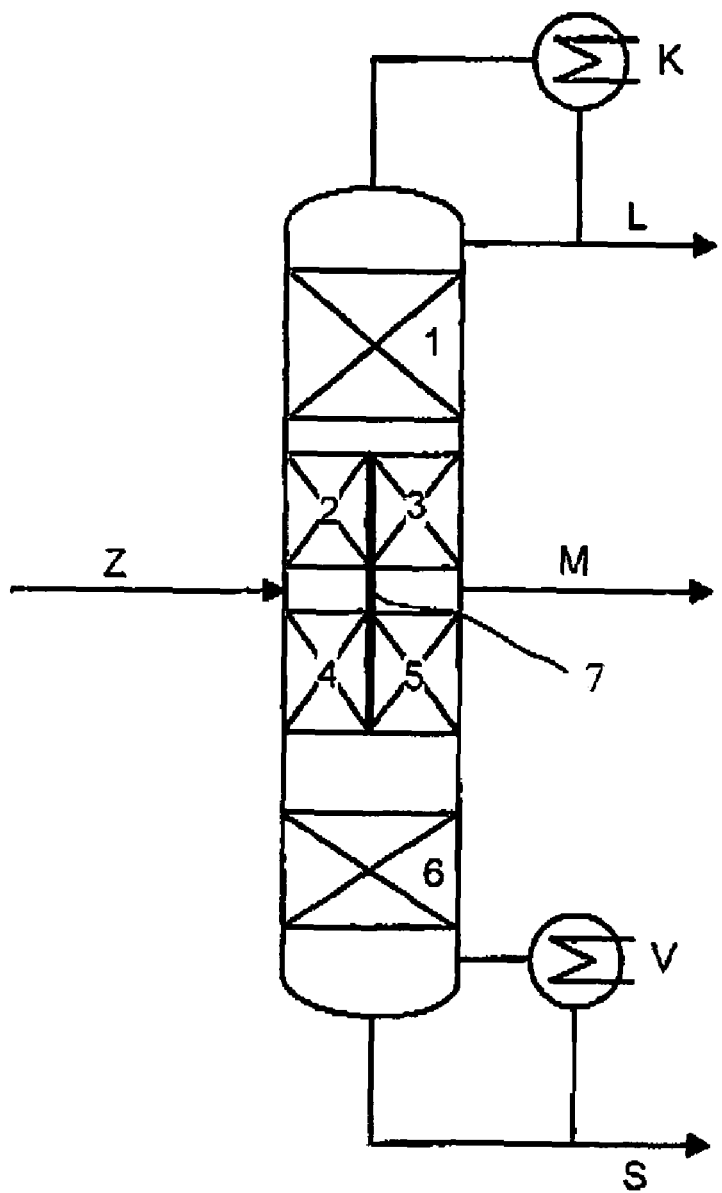
FIG. 1 is an example of a dividing wall column.

The present invention accordingly provides a continuously operated process for the purification by distillation of the 1,2-propylene glycol formed as by-product in the synthesis of propylene oxide, wherein the mixture formed in the synthesis which contains the 1,2-propylene glycol is separated in a dividing wall column into low-, intermediate- and high-boiling fractions and the 1,2-propylene glycol is taken off as intermediate boiler at the side offtake of the column.

The distillation process of the present invention enables the 1,2-propylene glycol to be isolated by distillation in high purity directly from the wastewater stream obtained in the synthesis of propylene. Compared to the distillation processes disclosed in the prior art, the new process of the present invention leads to a reduced outlay in terms of apparatus and energy costs combined with improved product quality. Furthermore, the dividing wall column has a particularly low energy consumption and thus offers advantages in terms of the energy requirement compared to a conventional column.

At the same time, the novel process achieves a large increase in value added, since the 1,2-propylene glycol formed as by-product in the propylene oxide synthesis and present in the wastewater stream can be isolated economically. The novel process is extremely advantageous for industrial use.

Distillation columns having side offtakes and a dividing wall, hereinafter also referred to as dividing wall columns, are known. They represent a further development of distillation columns which have only the side offtake but no dividing wall. The use of the last-named conventional type of column is, however, restricted because the products taken off at the side offtakes are never completely pure. In the case of products taken off at the side offtakes in the enrichment section of the column, which are usually taken off in liquid form, the side product still contains proportions of low-boiling components which should be separated off via the top. In the case of products taken off at side offtakes in the stripping section of the column, which are usually taken off in gaseous form, the side product still contains proportions of high boilers. The use of conventional side offtake columns is therefore restricted to cases in which contaminated side products are permissible.

When a dividing wall is installed in such a column, the separation action can be improved and it becomes possible for side products to be taken off in pure form. A dividing wall is installed in the middle region above and below the feed point and the side offtake. This can be fixed in place by welding or can be merely pushed into place. It seals off the offtake section from the inflow section and prevents cross-mixing of liquid and vapor streams over the entire column cross section in this part of the column. This reduces the total number of distillation columns required in the fractionation of multicomponent mixtures whose components have similar boiling points.

This type of column has been used, for example, for the separation of an initial mixture of the components methane, ethane, propane and butane (U.S. Pat. No. 2,471,134), for the separation of a mixture of benzene, toluene and xylene (U.S. Pat. No. 4,230,533) and for the separation of a mixture of n-hexane, n-heptane and n-octaue (EP 0 122 367).

Dividing wall columns can also be used successfully for separating mixtures which boil azeotropically (EP 0 133 510).

Finally, dividing wall columns in which chemical reactions can be carried out with simultaneous distillation of the products are also known. Examples which may be mentioned are esterifications, tansesterifications, saponifications and acetalizations (EP 0 126 288).

FIG. 1 schematically shows the isolation of the 1,2-propylene glycol formed as by-product in the synthesis of propylene oxide and present in the wastewater stream in a dividing wall column. Here, the wastewater stream from the propylene oxide synthesis is introduced as feed Z into the column. In the column, this wastewater stream is separated into a fraction comprising the low boilers L, which consists essentially of water and methoxypropanols, and a fraction comprising the high boilers S, which consists, among others, of dipropylene glycol and tripropylene glycol. The 1,2-propylene glycol can be taken off from the side offtake for intermediate boilers M.

To take off the product at the side offtake, it is possible to use receivers in which the liquid or the condensing vapor can be collected and which may be located either inside or outside the column.

To carry out the process of the present invention, it is possible to use customary dividing wall columns, for instance the columns described in the prior art.

Such a dividing wall column preferably has, for example, from 15 to 60, more preferably from 25 to 50, theoretical plates. The process of the present invention can be carried out particularly advantageously using such a design.

The upper, combined region 1 of the inflow and offtake part of the dividing wall column preferably has from 5 to 50%, more preferably from 15 to 30%, the enrichment section 2 of the inflow part preferably has from 5 to 50%, more preferably from 15 to 30%, the stripping section 4 of the inflow part preferably has from 5 to 50%, more preferably from 15 to 30%, the stripping section 3 of the oftake part preferably has from 5 to 50%, more preferably from 15 to 30%, the enrichment section 5 of the offtake part preferably has from 5 to 50%, more preferably from 15 to 30%, and the lower combined region 6 of the inflow and offtake part of the column preferably has from 5 to 50%, more preferably from 15 to 30%, in each case of the total number of theoretical plates in the column.

The sum of the number of theoretical plates in the regions 2 and 4 in the inflow part is preferably from 80 to 110%, more preferably from 90 to 100%, of the sum of the number of theoretical plates in the regions 3 and 5 in the offtake part.

It is likewise advantageous for the inlet for the feed and the side offtake to be arranged at different heights in the column relative to the position of the theoretical plates. The inlet is preferably located at a position which is from 1 to 8, more preferably from 3 to 5, theoretical plates above or below the side offtake.

The dividing wall column used in the process of the present invention is preferably configured either as a packed column containing random packing or ordered packing or as a tray column. For example, it is possible to use sheet metal or mesh packing having a specific surface area of from 100 to 1000 $m^2/m^3$, preferably from about 250 to 750 $m^2/m^3$, as ordered packing. Such packing provides a high separation efficiency combined with a low pressure drop per theoretical plate.

In the abovementioned configuration of the column, the region of the column divided by the dividing wall 7, which consists of the enrichment section 2 of the inflow part, the stripping section 3 of the offtake part, the stripping section 4 of the inflow part and the enrichment section 5, or parts thereof is preferably provided with ordered packing or random packing. The dividing wall can be thermally insulated in these regions.

The wastewater stream in which the high-boiling by-products are present together with the 1,2-propylene glycol is then introduced into the column in the form of the feed stream Z. This feed stream is generally liquid. However, it can be advantageous to subject this feed steam to preliminary vaporization and subsequently introduce it into the column as a two-phase, i.e. gaseous and liquid, mixture or in the form of one gaseous stream and one liquid stream. This preliminary vaporization is particularly useful when the feed stream contains relatively large amounts of low boilers. The preliminary vaporization enables a considerable load to be taken off the stripping section of the column.

The feed stream is advantageously metered by means of a pump or via a static inflow head of at least 1 m into the inflow part of the dividing wall column. This inflow is preferably regulated via a cascade regulation in combination with the regulation of the liquid level in the inflow part. The regulation is set so that the amount of liquid introduced into the enrichment section 2 cannot drop below 30% of the normal value. It has been found that such a procedure is important to even out troublesome fluctuations in the amount or concentration of the feed.

It is likewise important for the division of the liquid flowing down from the stripping section 3 of the offtake part of the column between the side offtake for intermediate boilers M and the enrichment section 5 of the offtake part to be set by means of a regulation device so that the amount of liquid going to the region 5 cannot drop below 30% of the normal value.

Adherence to these prerequisites has to be ensured by means of appropriate regulation methods.

Regulation mechanisms for the operation of dividing wall columns have been described, for example, in Chem. Eng. Technol. 10 (1987) 92-98, Chem.-Ing.-Technol. 61 (1989), No. 1, 16-25, Gas Separation and Purification 4 (1990) 109-114, Process Engineering 2 (1993) 33-34, Trans IChemE 72 (1994) Part A 639-644, Chemical Engineerng 7 (1997) 72-76. The regulation mechanisms described in this prior art can also be employed for or applied to the process of the present invention.

The regulation principle described below has been found to be particularly useful for the continuously operated purification of the 1,2-propylene glycol by distillation. It is readily able to cope with fluctuations in loading. The distillate is thus preferably taken off under temperature control.

A temperature regulation device which utilizes the downflow quantity, the reflux ratio or preferably the quantity of runback as regulating parameter is provided in the combined region 1 of the inflow and offtake part. The measurement point for the temperature regulation is preferably located from 3 to 8, more preferably from 4 to 6, theoretical plates below the upper end of the column.

Appropriate setting of the temperature then results in the liquid flowing down from the region 1 being divided at the upper end of the dividing wall so that the ratio of the liquid flowing to the inflow part to that flowing to the offtake part is preferably from 0.1 to 1.0, more preferably from 0.3 to 0.6.

In this method, the downflowing liquid is preferably collected in a receiver which is located in or outside the column and from which the liquid is then fed continuously into the column. This receiver can thus take on the task of a pump reservoir or provide a sufficiently high static head of liquid which makes it possible for the liquid to be passed on further in a regulated manner by means of regulating devices, for example valves. When packed columns are used, the liquid is firstly collected in collectors and from there conveyed to an internal or external receiver.

The vapor stream at the lower end of the dividing wall 7 is set by selection and/or dimensioning of the separation internals and/or incorporation of pressure-reducing devices, for example orifice plates, so that the ratio of the vapor stream in the inflow part to that in the offtake part is preferably from 0.8 to 1.2, preferably from 0.9 to 1.1.

In the abovementioned regulation principle, a temperature regulation device which utilizes the quantity taken off at the bottom as regulating parameter is provided in the lower combined region 6 of the inflow and offtake part. The bottom product can therefore be taken off under temperature control. The measurement point for the temperature regulation device is preferably located from 3 to 6, more preferably from 4 to 6, theoretical plates above the lower end of the column.

In addition, the level regulation in region 6 and thus for the bottom of the column can be utilized for regulating the quantity taken off at the side offtake. For this purpose, the liquid level in the vaporizer is used as regulating parameter.

The differential pressure over the column can also be utilized as regulating parameter for the heating power. The distillation is advantageously carried out at a pressure of from 5 to 500 mbar, preferably from 10 to 200 mbar. The pressure is measured at the top of the column. Accordingly, the heating power of the vaporizer V at the bottom of the column is selected to maintain this pressure range.

Under these pressure conditions, the distillation temperature is then in the range from 50 to 200° C., preferably from 80 to 150° C. The distillation temperature here is the temperature which is measured at the side offtake of the dividing wall column.

The pressure at the top of the column is thus from 5 to 500 mbar in the process of the present invention.

In addition, the distillation temperature at the side offtake is from 50 to 200° C. in the process of the present invention.

To be able to operate the dividing wall column in a trouble-free manner, the abovementioned regulation mechanisms are usually employed in combination.

In the separation of multicomponent mixtures into low-boiling, intermediate-boiling and high-boiling fractions, there are usually specifications in respect of the maximum permissible proportion of low boilers and high boilers in the middle fraction. Here, individual components which are critical to the separation problem, referred to as key components, or else the sum of a plurality of key components are/is specified.

Adherence to the specification for the high boilers in the intermediate-boiling fraction is preferably regulated via the division ratio of the liquid at the upper end of the dividing wall. The division ratio is set so that the concentration of key components for the high-boiling fraction in the liquid at the upper end of the dividing wall amounts to from 10 to 80% by weight, preferably from 30 to 50% by weight of the value which is to be achieved in the stream taken off at the side. The liquid division can then be set so that when the concentration of key components of the high-boiling fraction is higher, more liquid is introduced into the inflow part, and when the concentration of key components is lower, less liquid is introduced into the inflow part.

Accordingly, the specification for the low boilers in the intermediate-boiling fraction is regulated by means of the heating power. Here, the heating power in the vaporizer V is set so that the concentration of key components for the low-boiling fraction in the liquid at the lower end of the dividing wall amounts to from 10 to 80% by weight, preferably from 30 to 50% by weight, of the value which is to be achieved in the product taken off at the side. Thus, the heating power is set so that when the concentration of key components of the low-boiling fraction is higher, the heating power is increased, and when the concentration of key components of the low-boiling fraction is lower, the heating power is reduced.

The concentration of low and high boilers in the intermediate-boiling fraction can be determined by customary analytical methods. For example, infrared spectroscopy can be used for detection, with the compounds present in the reaction mixture being identified by means of their characteristic absorptions. These measurements can be carried out in-line directly in the column. However, preference is given to using gas-chromatographic methods. In this case, sampling facilities are then provided at the upper and lower end of the dividing wall. Liquid or gaseous samples can then be taken continuously or at intervals from the column and analyzed to determine their compositions. The appropriate regulation mechanisms can then be activated as a function of the composition.

It is an objective of the process of the present invention to provide 1,2-propylene glycol having a purity of preferably at least 99%, more preferably 99.5%, with the sum of desired product and the key components present therein being 100% by weight.

The concentration of the key components of the low boilers (e.g. water, methoxypropanol, hydroxyacetone) and the key components of the high boilers (e.g. dipropylene glycol and tripropylene glycol) in the desired product should then preferably be below 1% by weight, more preferably below 0.5% by weight.

In a specific embodiment of the dividing wall column, it is also possible for the inflow part and offtake pant which are separated from one another by the dividing wall 7 not to be present in one column but to be physically separate from one another. In this specific embodiment, the dividing wall column can thus comprise at least two physically separate columns which then have to be thermally coupled with one another. Such thermally coupled columns exchange vapor and liquid between them, but energy is introduced via only one column. This specific embodiment has the advantage that the thermally coupled columns can also be operated under different pressures, which can make it possible to achieve better setting of the temperature level required for the distillation than in the case of a conventional dividing wall column.

Figure 2:
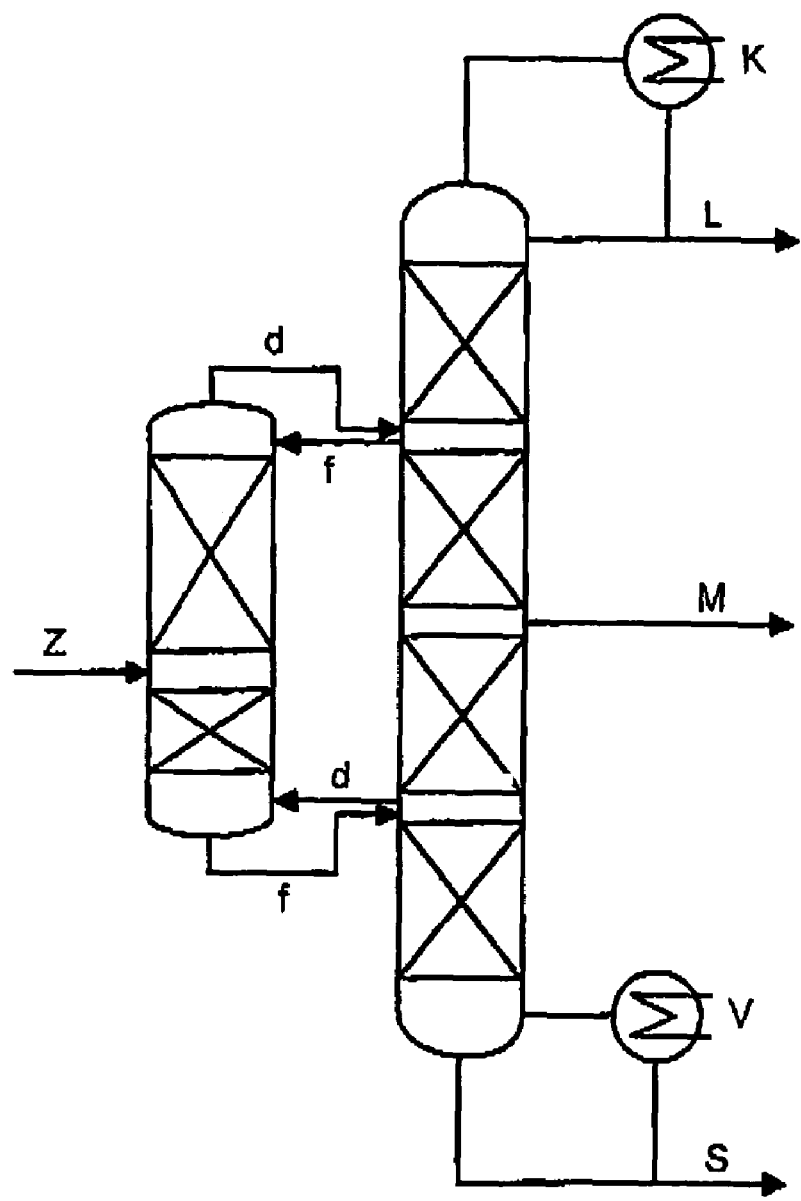
FIG. 2 is an example of a dividing wall column comprising two physically separate columns thermally coupled with one another.
Figure 3:
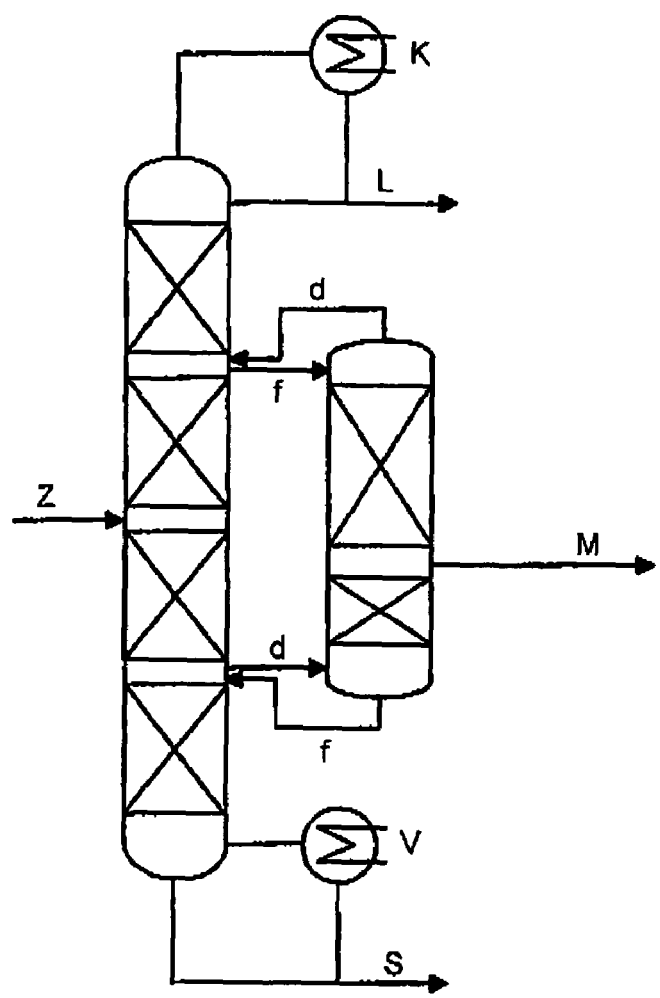
FIG. 3 is another example of a dividing wall column comprising two physically separate columns thermally coupled with one another.

Examples of dividing wall columns in the specific embodiment of thermally coupled columns are shown schematically in FIGS. 2 and 3.

FIG. 2 shows a variant in which energy is introduced via the vaporizer V of the column which is located downstream of the column via which the wastewater steam is fed in as feed Z. In this arrangement, the wastewater stream is firstly separated into a low-boiling fraction and a high-boiling fraction, each of which also contains intermediate boilers, in the first column. The resulting fractions are subsequently transferred to the second column, with the low-boiling fraction comprising intermediate boilers being fed in at the upper end of the second column and the high-boiling fraction comprising intermediate boilers being fed in at the lower end. The low boilers L are distilled off via the top of the column and isolated via the condenser K. The high boilers S are obtained in the bottoms from the column. The high-purity 1,2-propylene glycol can be taken off at the side offtake for intermediate boilers M. The two columns can exchange vapor and liquid via d and f.

FIG. 3 shows a further variant of thermally coupled columns. In this embodiment, the energy is introduced via the vaporizer V of the column into which the wastewater stream is also fed as feed Z. The low boilers L are distilled off via the top of this column and are condensed by means of the condenser K. The high boilers S are obtained in the bottoms. Low boilers L enriched with intermediate boilers are then transferred to the upper part of the downstream column and high boilers S enriched with intermediate boilers are transferred to the lower part of the downstream column. The high-purity 1,2-propylene glycol can be taken off from the side offtake for intermediate boilers M. The two columns can exchange vapor and liquid via d and f.

The columns of FIGS. 2 and 3 can also be configured as packed columns containing random packing or ordered packing or as tray columns. For example, sheet metal or mesh packing having a specific surface area of from 100 to 1000 $m^2/m^3$, preferably from about 250 to 750 $m^2/m^3$, can be used as ordered packing. Such packing provides a high separation efficiency combined with a low pressure drop per theoretical plate.

The propylene oxide synthesis which provides the feed for the process of the present invention for the continuously operated purification by distillation of the 1,2-propylene glycol formed as by-product in the coproduct-free propylene oxide synthesis in a dividing wall column can be carried out using the hydroperoxides known from the prior art.

Examples of such hydroperoxides are tert-butyl hydroperoxide and ethylbenzene hydroperoxide. Preference is given to using hydrogen peroxide as hydroperoxide for the propylene oxide synthesis, and this can also be used as an aqueous hydrogen peroxide solution.

The preparation of hydrogen peroxide can be carried out using, for example, the anthraquinone process by means of which virtually the entire world production of hydrogen peroxide is produced. This process is based on the catalytic hydrogenation of an anthraquinone compound to form the corresponding anthrahydroquinone compound, subsequent reaction of this with oxygen to form hydrogen peroxide and subsequent extraction to separate off the hydrogen peroxide formed. The catalysis cycle is closed by renewed hydrogenation of the anthraquinone compound which is obtained back.

An overview of the anthraquinone process is given in "Ullmanns Encyclopedia of Industrial Chemistry", 5th Edition, Volume 13, pages 447 to 456.

It is likewise conceivable to obtain hydrogen peroxide by converting sulfuc acid into peroxodisulfuric acid by anodic oxidation with simultaneous evolution of hydrogen at the cathode. Hydrolysis of the peroxodisulfuric acid then leads via peroxomonosulfuric acid to hydrogen peroxide and sulfuric acid, which is thus recovered.

It is of course also possible to prepare hydrogen peroxide from the elements.

In the synthesis of propylene oxide from the hydroperoxide and propylene, one or more suitable catalysts can be added to increase the efficiency of the reaction. Here, heterogeneous catalysts are preferably used.

All heterogeneous catalysts which are suitable for the respective reaction are conceivable. Preference is given to using catalysts which comprise a porous oxidic material, e.g. a zeolite. The catalysts used preferably comprise a titanium-, germanium-, tellurium-, vanadium-, chromium-, niobium- or zirconium-containing zeolite as porous oxidic material.

Specific mention may be made of titanium-, gerium-, tellurium-, vanadium-, chromium-, niobium- and zirconium-containing zeolites having a pentasil zeolite structure, in particular the types which can be assigned X-ray-crystallographically to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG, ZON structure or to mixed structures comprising two or more of the abovementioned structures. Furthermore, titanium-containing zeolites having the ITQ-4, SSZ-24, TTM-1, UTD-1, CIT-1 or CIT-5 structure are also conceivable for use in the process of the present invention. Further titanium-containing zeolites which may be mentioned are those of the ZSM48 or ZSM-12 structure.

Particular preference is given to Ti zeolites having an MFI or MEL structure or an MFI/MEL mixed structure. Very particlar preference is given to the titanium-containing zeolite catalysts which are generally referred to as "TS-1", "TS-2", "TS-3" and also Ti zeolites having a framework structure isomorphous with β-zeolite.

The use of a heterogeneous catalyst comprising the titanium-containing silicalite TS-1 is very advantageous.

It is possible to use the porous oxidic material itself as catalyst. However, it is of course also possible for the catalyst used to be a shaped body comprising the porous oxidic material. All processes known from the prior art can be used for producing the shaped body from the porous oxidic material.

Noble metals in the form of suitable noble metal components, for example in the form of water-soluble salts, can be applied to the catalyst material before, during or after the one or more shaping steps in these processes. This method is preferably employed for producing oxidation catalysts based on titanium silicates or vanadium silicates having a zeolite structure, and it is thus possible to obtain catalysts which contain from 0.01 to 30% by weight of one or more noble metals from the group consisting of ruthenium, rhodium, palladium, osmium, iridium, platinum, rhenium, gold and silver. Such catalysts are described, for example, in DE-A 196 23 609.6.

Of course, the shaped bodies can be processed further. All methods of comminution are conceivable, for example splitting or crushing the shaped bodies, as are further chemical treatments as are described above by way of example.

When a shaped body or a plurality thereof is/are used as catalyst, it/they can, after deactivation has occurred in the process of the present invention, be regenerated by a method in which the deposits responsible for deactivation are burned off in a targeted manner. This is preferably carried out in an inert gas atmosphere containing precisely defined amounts of oxygen-donating substances. This regeneration process is described in DE-A 197 23 949.8. It is also possible to use the regeneration processes mentioned there in the discussion of the prior art.

As solvents, it is possible to use all solvents which completely or at least partly dissolve the starting materials used in the oxirane synthesis. Examples of solvents are aliphatic, cycloaliphatic and aromatic hydrocarbons, esters, ethers, amides, sulfoxides and ketones and also alcohols. The solvents can also be used in the form of mixtures. Preference is given to using alcohols. The use of methanol as solvent is particularly preferred.

In general, the reaction temperature in the preparation of the propylene oxide in steps (i) and (iii) is in the range from 0 to 120° C., preferably in the range from 10 to 100° C. and more preferably in the range from 20 to 90° C. The pressures which occur range from 1 to 100 bar, preferably from 1 to 40 bar, more preferably from 1 to 30 bar. Preference is given to employing pressures under which no gas phase is present.

The concentration of propylene and hydrogen peroxide in the feed stream is generally selected so that the molar ratio is preferably in the range from 0.7 to 20, more preferably in the range from 0.8 to 5.0, particularly preferably in the range from 0.9 to 2.0 and in particular in the range from 1.0 to 1.6.

To reduce the hydroperoxy alcohols present in the product mixture from the preparation of propylene oxide, it is possible to employ the methods described in DE 101 05 527.7.

For example, it is possible to use phosphorus(III) compounds, for example phosphorus trichloride, phosphines (e.g. triphenylphosphine, tributylphosphine), phosphorous acid or its salts or sodium hypophosphite.

Reduction using sulfur(II) compounds such as hydrogen sulfide or salts thereof, sodium polysulfides, dimethyl sulfide, tetrahydrothiophene, bis(hydroxyethyl) sulfide or sodium thiosulfate or using sulfur(IV) compounds such as sulfurous acid and its salts, sodium bisulfite or thiourea S-oxide is also possible.

Further reducing agents are nitrites, for example sodium nitrite or isoamyl nitrite, α-Hydroxycarbonyl compounds such as hydroxyacetone, dihydroxyacetone, 2-hydroxycyclopentanone (glutaroin), 2-hydroxycyclohexanone (adipoin), glucose and other reducing sugars are also suitable. Enediols such as ascorbic acid or compounds which contain a boron-hydrogen bond, for example sodium borohydride or sodium cyanoborohydride, can likewise be used.

However, catalytic hydrogenation processes using hydrogen, which can be carried out in a homogeneous or heterogeneous phase, are preferably chosen for the reduction of product mixtures containing α-hydroperoxy alcohols. The hydrogenation catalyst used here comprises at least one active metal from transition groups VIIb, VIII, Ia and Ib of the Periodic Table of the Elements, either individually or as a mixture of two or more thereof. For example, it is possible to use palladium (Pd), platinum (Pt), rhodium (Rh), ruthenium (Ru), iridium (Ir), osmium (Os), iron (Fe), cobalt (Co), nickel (Ni) and/or copper (Cu), preferably Pd, Pt, Rh, Ru and Ir, particularly preferably Pd. These catalysts can be used either in powder form or as active metal bodies. Preference is given to using foils, wires, meshes, granules and crystallite powder produced from at least one active metal or a mixture of two or more thereof. Furthermore, active metal oxides can also be used, for example as suspensions of at least one active metal or a mixture of two or more thereof.

As reactors for the propylene oxide synthesis, it is of course possible to use all conceivable reactors which are best suited to the respective reactions. A reactor is not restricted to an individual vessel for the propylene oxide synthesis. Rather, it is also possible to use, for example, a cascade of stirred vessels.

Fixed-bed reactors are preferably used as reactors for the propylene oxide synthesis. Further preference is given to using fixed-bed tube reactors as fixed-bed reactors.

In the above-described propylene oxide synthesis by reaction of propylene with a hydroperoxide which is preferably employed, particular preference is given to using an isothermal fixed-bed reactor as reactor for step (i) and an adiabatic fixed-bed reactor for step (iii), with the hydroperoxide being separated off in step (ii) by means of a separation apparatus.

Thus, the wastewater stream which comprises 1,2propylene glycol and is used as feed to the process of the present invention is preferably obtained from an isothermal fixed-bed reactor and an adiabatic fixed-bed reactor in the preparation of propylene oxide.

In the preparation of propylene oxide, the residence times in the reactor or reactors depend essentially on the desired conversions. In general, they are less than 5 hours, preferably less than 3 hours, more preferably less than 1 hour and particularly preferably about half an hour.

It is also conceivable to use a plurality of hydroperoxides for the reaction. If propylene and/or a plurality of hydroperoxides are reacted with one another in the respective steps, various products resulting from the reactions can be present in the mixtures. However, the 1,2-propylene glycol can also be obtained successfully from such mixtures by purification by distillation in the process of the present invention.

In a preferred embodiment of the propylene oxide synthesis, hydrogen peroxide is used as hydroperoxide and propylene is brought into contact with a heterogeneous catalyst during the reaction.

The invention also provides an apparatus for carrying out a continuously operated process for the purification by distillation of the 1,2-propylene glycol formed as by-product in the synthesis of propylene oxide, which comprises at least one reactor for preparing propylene oxide and at least one dividing wall column for purifying the 1,2-propylene glycol by distillation.

In a specific embodiment, the apparatus for carrying out a continuously operated process for the purification by distillation of the 1,2-propylene glycol formed as by-product in the synthesis of propylene oxide comprises at least one isothermal reactor and one adiabatic reactor for steps (i) and (iii) and a separation apparatus for step (ii) for preparing propylene oxide and at least one dividing wall column for purifying the 1,2-propylene glycol by distillation.

In a specific embodiment of the apparatus, the dividing wall column can also comprise at least two thermally coupled columns.

The invention is illustrated by the following example.

EXAMPLE

The coproduct-free preparation of propylene oxide from propylene and hydrogen peroxide by the process described in WO 00/07965 produced a wastewater stream which contained 1,2-propylene glycol and had the following composition:
about 10% by weight of low-boiling components includng the key components water, methoxypropanols, hydroxyacetone,
about 85% by weight of 1,2-propylene glycol, and
about 5% by weight of high-boiling components including the key components dipropylene glycol and tripropylexe glycol.

This mixture was distilled with the aid of a dividing wall column into which the mixture was continuously fed. The 1,2-propylene glycol was taken off as intermediate boiler from the side offtake of the column. The objective of the distillation was to purify the 1,2-propylene glycol so as to reduce the total content of impurities to below 1% by weight. For this purpose, the heating power of the bottom vaporizer was regulated so that the total concentration of the key components in the product taken off at the side was less than 1% by weight.

The required energy content of the distillation was used as a measure of the effectiveness of the separation. It was calculated by dividing the vaporizer power by the mass throughput per hour. As column configurations, the arrangements shown in the table were selected:

| Column configuration | Energy requirement/(kg/h) [kW/(kg/h)] | Energy saving [%] |
|---|---|---|
| Conventional column with side offtake | 0.99 | — |
| Two conventional columns connected in series | 0.90 | 9.1 |
| Dividing wall column | 0.73 | 26.3 |

It is clear that the dividing wall configuration had a considerable energy advantage over the two conventional distillation arrangements, since the energy requirement for the distillation of the desired product was significantly lower than for the distillation in the conventional distillation columns.

LIST OF REFERENCE NUMERALS FOR FIGS. 1, 2 and 3:

1 Combined region of the inflow and offtake part of the dividing wall column
2 Enrichment section of the inflow part
3 Stripping section of the offtake part
4 Stripping section of the inflow part
5 Enrichment section of the offtake part
6 Combined region of the inflow and offtake part
7 Dividing wall
Z Feed
L Low boilers
M Side offtake for intermediate boilers
S High boilers
K Condenser
V Vapoizer
d Vapor
f Liquid Horizontal and diagonal or indicated diagonal lines in the columns symbolize packing made up of random packing elements or ordered packing which may be present in the column.

The invention claimed is:

1. A continuously operated process for the purification by distillation of the 1,2-propylene glycol formed as by-product in the synthesis of propylene oxide, wherein the mixture formed in the synthesis which contains the 1,2-propylene glycol is separated in a dividing wall column into low-, intermediate- and high-boiling fractions and the 1,2-propylene glycol is taken off as intermediate boiler at the side offtake of the column.

2. The process as claimed in claim 1, wherein the dividing wall colunm consists of at least two thermally coupled columns.

3. The process as claimed in claim 1, wherein the dividing wall column has from 15 to 60 theoretical plates.

4. The process as claimed in claim 1, wherein the pressure at the top of the dividing wall column is from 5 to 500 mbar.

5. The process as claimed in claim 1, wherein the distillation temperature at the side offtake of the dividing wall column is from 50 to 200° C.

6. The process as claimed in claim 1, wherein the sum of the key components in the purified 1,2-propylene glycol is less than 1% by weight, with the sum of 1,2-propylene glycol and key components being 100% by weight.

7. The process as claimed in claim 1, wherein the dividing wall column has from 15 to 60 theoretical plates, the pressure at the top of the dividing wall column is from 5 to 500 mbar and the distillation temperature at the side offtake of the dividing wall column is from 50 to 200° C.

8. The process as claimed in claim 7, wherein the sum of the key components in the purified 1,2-propylene glycol is less than 1% by weight, with the sum of 1,2-propylene glycol and key components being 100% by weight.

9. The process as claimed in claim 1, wherein the mixture containing 1,2-propylene glycol is prepared in a process comprising at least the steps (i) to (iii):
  (i) reaction of the hydroperoxide with propylene to give a product mixture comprising propylene oxide and unreacted hydroperoxide,
  (ii) separation of the unreacted hydroperoxide from the mixture resulting from step (i),
  (iii) reaction of the hydroperoxide which has been separated off in step (ii) with propylene.

10. The process as claimed in claim 9, wherein an isothermal fixed-bed reactor is used in step (i), an adiabatic fixed-bed reactor is used in step (iii) and a separation apparatus is used in step (ii).

11. The process as claimed in claim 9, wherein hydrogen peroxide is used as hydroperoxide and propylene is brought into contact with a heterogeneous catalyst during the reaction.

12. A continuously operated process for the purification by distillation of the 1,2-propylene glycol formed as by-product in the synthesis of propylene oxide, wherein the mixture formed in the synthesis which contains the 1,2-propylene glycol is separated in a dividing wall column into low-, intermediate- and high-boiling fractions and the 1,2-propylene glycol is taken off as intermediate boiler at the side offtake of the column, and wherein the mixture containing 1,2-propylene glycol is prepared in a process comprising at least the steps (i) to (iii):
  (i) reaction of the hydroperoxide with propylene to give a product mixture comprising propylene oxide and unreacted hydroperoxide,
  (ii) separation of the unreacted hydroperoxide from the mixture resulting from step (i),
  (iii) reaction of the hydroperoxide which has been separated off in step (ii) with propylene.

13. The process as claimed in claim 12, wherein the dividing wall column has from 15 to 60 theoretical plates, the pressure at the top of the dividing wall column is from 5 to 500 mbar and the distillation temperature at the side offtake of the dividing wall column is from 50 to 200° C.

14. The process as claimed in claim 12, wherein the sum of the key components in the purified 1,2-propylene glycol is less than 1% by weight, with the sum of 1,2-propylene glycol and key components being 100% by weight.

15. The process as claimed in claim 12, wherein an isothermal fixed-bed reactor is used in step (i), an adiabatic fixed-bed reactor is used in step (iii) and a separation apparatus is used in step (ii).

16. The process as claimed in claim 12, wherein hydrogen peroxide is used as hydroperoxide and propylene is brought into contact with a heterogeneous catalyst during the reaction.

17. A continuously operated process for the purification by distillation of the 1,2-propylene glycol formed as by-product in the synthesis of propylene oxide, wherein the mixture formed in the synthesis which contains the 1,2-propylene glycol is separated in a dividing wall column into low-, intermediate- and high-boiling fractions and the 1,2-propylene glycol is taken off as intermediate boiler at the side offtake of the column, and wherein the mixture containing 1,2-propylene glycol is prepared in a process comprising at least the steps (i) to (iii):
  (i) reaction of the hydrogen peroxide with propylene in an isothermal fixed-bed reactor to give a product mixture comprising propylene oxide and unreacted hydroperoxide, where propylene is brought into contact with a heterogeneous catalyst during the reaction,
  (ii) separation of the unreacted hydrogen peroxide from the mixture resulting from step (i) in a separation apparatus,
  (iii) reaction of the hydrogen peroxide which has been separated off in step (ii) with propylene in an adiabatic fixed-bed reactor,
  wherein the dividing wall column has from 15 to 60 theoretical plates, the pressure at the top of the dividing wall column is from 5 to 500 mbar and the distillation temperature at the side offtake of the dividing wall column is from 50 to 200° C., and wherein the sum of the key components in the purified 1,2-propylene glycol is less than 1% by weight, with the sum of 1,2-propylene glycol and key components being 100% by weight.

* * * * *